United States Patent [19]

Kurose

[11] Patent Number: 4,570,636

[45] Date of Patent: Feb. 18, 1986

[54] METHOD OF ELECTRICALLY SYNTHESIZING SENSE OF TASTE

[76] Inventor: Isoji Kurose, Iwakuni 3958-13, Tsurumiku, Beppu-shi, 874, Japan

[21] Appl. No.: 617,881

[22] Filed: Jun. 6, 1984

[30] Foreign Application Priority Data

Jun. 10, 1983 [JP] Japan ................... 58-104006

[51] Int. Cl.⁴ ............................................. A61N 1/00
[52] U.S. Cl. ................... 128/419 R; 128/787; 128/420 R
[58] Field of Search ............... 128/419 R, 420 A, 787

[56] References Cited

U.S. PATENT DOCUMENTS 3,958,577  5/1976  Rodler .......................... 128/420 A
4,334,542  6/1982  Takinishi et al. .................. 128/787

FOREIGN PATENT DOCUMENTS 651951  4/1951  United Kingdom .......... 128/420 A

Primary Examiner—William E. Kamm
Attorney, Agent, or Firm—Wegner & Bretschneider

[57] ABSTRACT

A method of electrically synthesizing the sense of taste includes a step of previously determining respective time-varying, gustatory potential curves of the saltiness, bitterness, sweetness, and sourness, a step of generating first and second voltage outputs having substantially the same time-potential characteristics as respective gustatory potential curves of the saltiness and bitterness; and a step of combining voltages sampled from the first and second voltage outputs so that a potential curve formed of the sampled voltages has substantially the same time-potential characteristics as the gustatory potential curve of one selected from the sweetness and sourness, to form a third voltage output indicating the selected one of the sweetness and sourness.

3 Claims, 14 Drawing Figures

METHOD OF ELECTRICALLY SYNTHESIZING SENSE OF TASTE

BACKGROUND OF THE INVENTION

The present invention relates to a method of electrically synthesizing the sense of taste, and more particularly to a method of electrically generating or synthesizing four fundamental qualities of taste, that is, the saltiness, bitterness, sweetness and sourness.

The present inventor formerly invented a method of electrochemically measuring the quality of taste, which is disclosed in a Japanese Patent Application (Laid-open No. 101,397/1979). In this method, attention is paid to the fact that the gustatory function of human beings is similar to the function of a galvanic cell, and the quality of taste of a substance capable of exciting the gustatory sense is determined by using a galvanic cell which contains a dielectric solution corresponding to saliva and is provided with a pair of electrodes immersed in the dielectric solution. That is, an aqueous solution of the above substance is added to the dielectric solution, and the waveform of the potential difference produced between the electrodes (namely, the so-called gustatory potential curve) is measured to determine the quality of taste of the substance.

As to gustatory potential curves obtained by the above galvanic cell and four fundamental qualities of taste, the following facts have been known.

(1) Of the four qualities of taste, the saltiness and bitterness are the fundamental taste. The sweetness and sourness can be obtained by synthesizing the saltiness and bitterness.

Figure 1A:
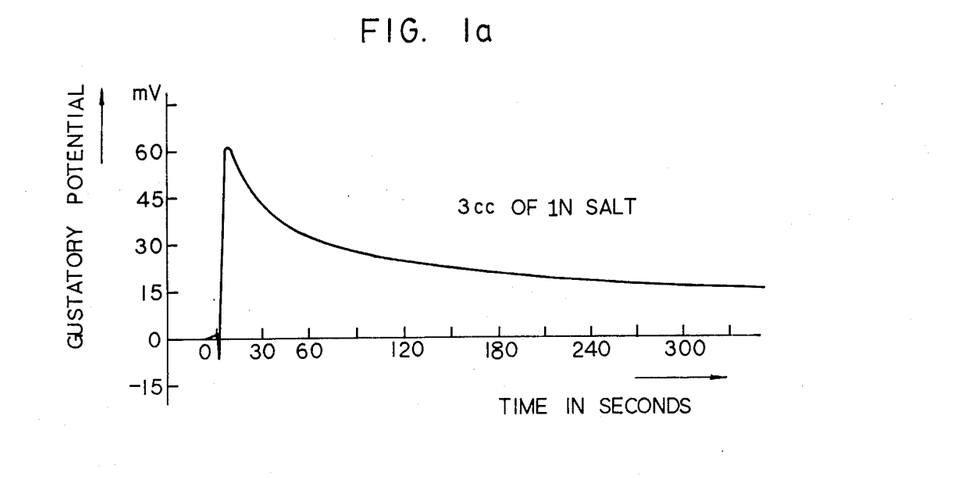
FIGS. 1a, 1b, 1c, and 1d show gustatory potential curves of the saltiness, bitterness, sweetness and sourness, respectively.

(2) The potential curve corresponding to the saltiness has a waveform such as shown in FIG. 1a. The saltiness is sensed at the rising portion of this curve, and is strongly sensed when the time constant of the curve lies in a range from 1.5931 to 0.7963. The 3 dB upper frequency, as defined hereinafter, corresponding to such a time constant lies in a range from 0.0999 to 0.1998 Hz, and a region where the saltiness is very strongly sensed, exists in the vicinity of 0.1 Hz.

A CR circuit having a series or parallel connection of capacitance C and resistance R gives an impedance Z which is a function of $\omega CR$, where $\omega = 2\pi f$, f is a frequency of the current applied thereto. The value of Z is the maximum when $\omega = 0$ and $$\frac{1}{\sqrt{2}}$$

of the maximum value when $\omega = \omega_h$ or $f = f_h$. The frequency $f_h$ is called as "3 dB upper frequency". That is, the gain of the CR circuit is decreased by 3 dB with respect to a current of the 3 dB upper frequency applied thereto as compared with the gain of the CR circuit with respect to a DC current.

Figure 1B:
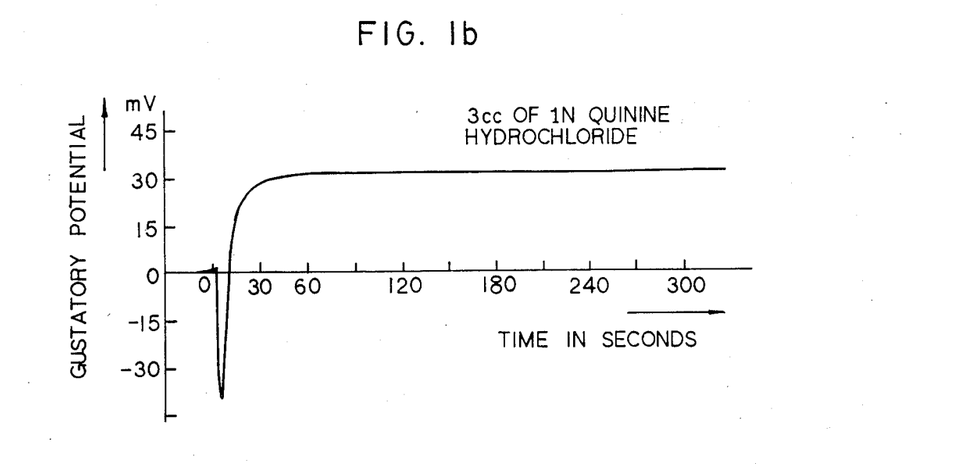

(3) The potential curve corresponding to the bitterness has a waveform such as shown in FIG. 1b. The bitterness is sensed at the falling portion of this curve, and is strongly sensed when the time constant of the curve lies in a range from 0.8337 to 0.4762. The 3 dB upper frequency corresponding to such a time constant lies in a range from 0.1909 to 0.3342 Hz. According to actual measurement, however, a region where the bitterness is very strongly sensed, exists in the vicinity of 0.35 Hz.

Figure 1C:
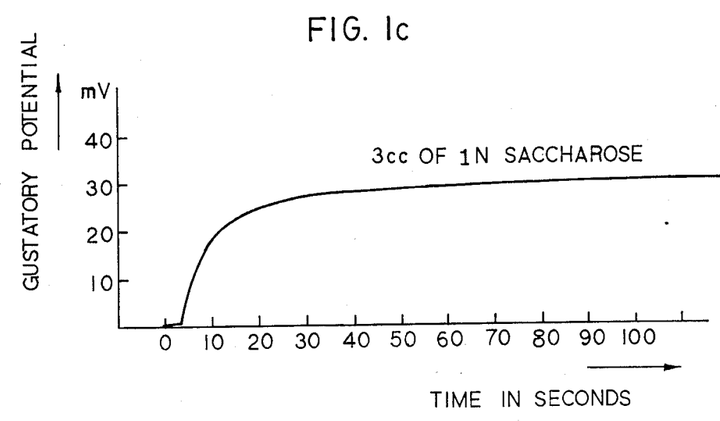

(4) The sweetness is a quality of taste which is obtained when the saltiness and bitterness coexists and moreover are mixed in a frequency region near 0.35 Hz (namely, the center of the frequency region where the bitterness is very strongly sensed). The potential curve corresponding to the sweetness has such a waveform as shown in FIG. 1C, and the rising portion of this curve has a relatively gentle slope. The sweetness is strongly sensed when the time constant of the curve lies in a range from 10.2645 to 18.7266. The 3 dB upper frequency corresponding to such a time constant lies in a range from 0.0155 to 0.0087 Hz.

Figure 1D:
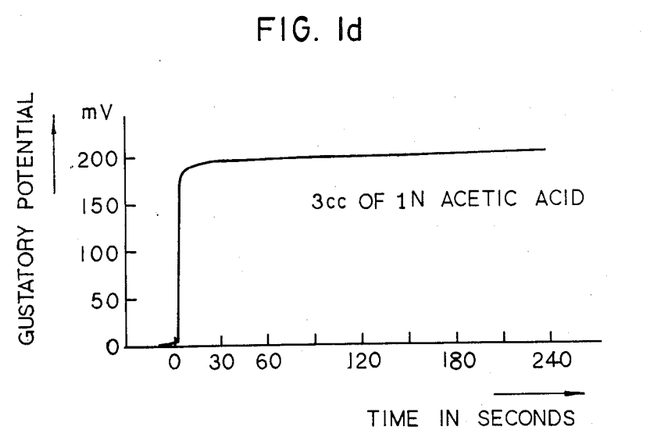

(5) The sourness is a quality of taste which is obtained when the saltiness and bitterness coexist and moreover are mixed in a frequency range near 0.1 Hz (namely, the center of the frequency range where the saltiness is very strongly sensed). The potential curve corresponding to the sourness has such a waveform as shown in FIG. 1d, and the rising portion of this curve has a steep slope. The sourness is strongly sensed when the time constant of the curve lies in a range from 5.1023 to 3.0722, and the 3 dB upper frequency corresponding to such a time constant lies in a range from 0.0317 to 0.0518 Hz.

(6) The boundary frequency between the sweetness and sourness lies in the vicinity of 0.15 Hz.

These facts have been found on the basis of the invention disclosed in the previously-referred Japanese Patent Application, that is, the invention that the four fundamental qualities of taste can be electrically measured by using a galvanic cell. The gustatory sense of human beings is basically caused by an electric stimulus which is generated by a galvanic cell. In view of this fact, the present invention has been made on the basis of the thought that a person may feel the same sense as given by a substance capable of producing a taste, when an electric stimulus is given to the person. If the same gustatory sense as given by the substance having a taste can be generated by the electric stimulus, such generation of gustatory sense will be used in various fields such as the analysis of various kinds of tastes and the diagnosis of gustatory function of human beings. That is, electronics will be utilized in the study of gustatory sense which is behind the studies of visual sense, auditory sense and others, and thus a great industrial effect will be expected.

SUMMARY OF THE INVENTION

It is accordingly an object of the present invention to provide a method of electrically generating and synthesizing the sense of taste.

According to the present invention, there is provided a method of electrically synthesizing the sense of taste, in which respective time-varying, gustatory potential curves of the saltiness, bitterness, sweetness and sourness are previously determined, first and second voltage outputs having substantially the same time-potential characteristics as respective gustatory potential curves of the saltiness and bitterness are generated, and voltage values sampled from the first and second voltage outputs are combined so that a potential curve formed of the sampled voltage values has substantially the same time-potential characteristics as the previously-determined gustatory potential curve of one selected from the sweetness and sourness, to obtain a third voltage output indicating the selected one of the sweetness and sourness.

DESCRIPTION OF THE PREFERRED EMBODIMENT

The potential curves which are shown in FIGS. 1a to 1d and are obtained in such a manner that each of substances capable of producing the four fundamental qualities of taste is added to the dielectric solution (namely, the electrolytic solution) in the galvanic cell, can be expressed by the following equations:

$$V_1 = K_1 \epsilon^{-\frac{t}{\tau_1}} \cdot t \quad \text{for saltiness} \quad (1)$$

$$V_2 = K_2 \epsilon^{-\frac{t}{\tau_2}} \left(1 - \epsilon^{-\frac{t}{\tau_2}}\right) \quad \text{for bitterness} \quad (2)$$

$$V_3 = K_3 \left(1 - \epsilon^{-\frac{t}{\tau_3}}\right) \quad \text{for sweetness} \quad (3)$$

$$V_4 = K_4 \left(1 - \epsilon^{-\frac{t}{\tau_4}}\right) \quad \text{for sourness} \quad (4)$$

where $\tau_1 = (CR)_1$, $\tau_2 = (CR)_2$, $\tau_3 = (CR)_3$, and $\tau_4 = (CR)_4$ In actual measurement, 1N aqueous solutions of salt, quinine hydrochloride, saccharose, and acetic acid were used as substances producing the saltiness, bitterness, sweetness, and sourness, respectively, to obtain the above potential curves, and constants in the above equations were determined from the measured potential curves. Then, voltage waveforms given by the equations (1) to (4) were electrically formed, and were applied to the lingual papilla of a person. As regards the saltiness and bitterness, the same gustatory sense as given by the substance having the saltiness or bitterness was obtained. However, as regards the sweetness and sourness, the same gustatory sense as given by the substance having the sweetness or sourness was not obtained, but a taste similar to the saltiness was sensed when one of the voltage waveforms according to the equations (3) and (4) was applied to the lingual papilla. The reasons for this are as follows.

Figure 2:
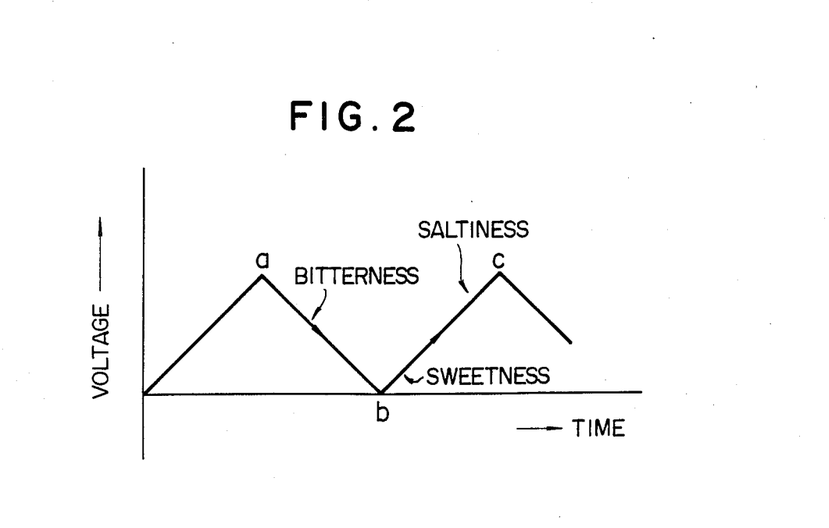
FIG. 2 is a graph for explaining the relationship between a gustatory potential curve and the generation of gustatory sense.

Now, let us use a triangular wave having a frequency of 0.1 to 0.35 Hz at which a clear gustatory sense is obtained, in place of the gustatory potential curves shown in FIGS. 1a to 1d, and apply a voltage waveform shown in FIG. 2 to the lingual papilla of a person. Then, the bitterness is sensed in the falling portion between points a and b. In the initial part of the rising portion between the point b and a point c, the bitterness is combined with the saltiness, and thus the sweetness is sensed. In the later part of the above rising portion, the bitterness is extinguished, and the saltiness is sensed. Thus, it is proved that the sweetness is obtained by combining the saltiness and bitterness. Similarly, the sourness can be obtained by combining the saltiness and bitterness. However, it depends upon a composite waveform whether the taste obtained by combining the saltiness and bitterness is the sweetness or sourness. It has been found by the following experiments that the sweetness is sensed when the rising portion of the composite waveform has a gentle slope as shown in FIG. 1c, and the sourness is sensed when the above rising portion has a steep slope as shown in FIG. 1d.

Figure 3A:
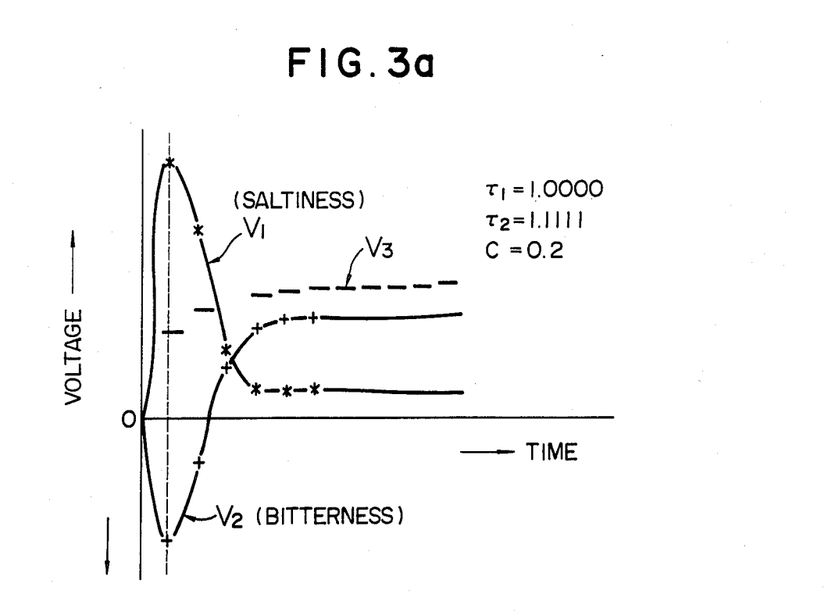
FIGS. 3a and 3b are graphs for explaining the principle on which the sweetness and bitterness are electrically synthesized.
Figure 3B:
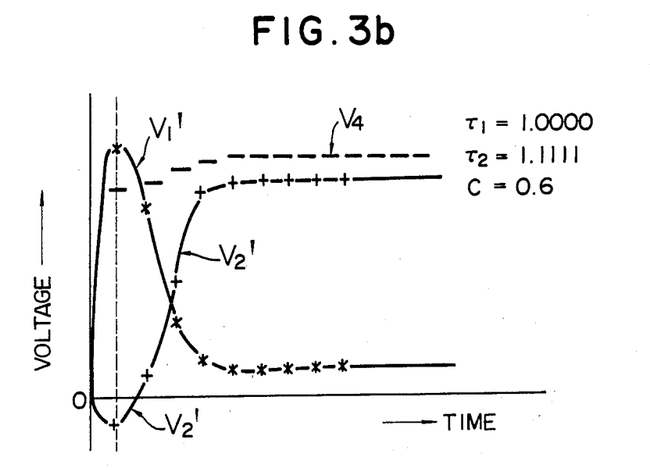

That is, in the case where a voltage waveform $V_1$ indicating the saltiness and a voltage waveform $V_2$ indicating the bitterness are produced so as to form a composite waveform $V_3$ shown in FIG. 3a, and the voltage waveforms $V_1$ and $V_2$ are applied in combination to the lingual papilla of a person, the sweetness is sensed. In this case, the voltage waveforms $V_1$ and $V_2$ correspond to the equations (1) and (2) in which the constants $\tau_1$, $\tau_2$, C, $K_1$ and $K_2$ are made equal to 1.0000, 1.1111, 0.2, 13.5 and 12.2, respectively. Further, voltage waveforms similar to the voltage waveforms $V_1$ and $V_2$ are obtained even when the value of the constant c is changed over a range from 0 to 0.2. In the case where a voltage waveform $V_1'$ indicating the saltiness and a voltage waveform $V_2'$ indicating the bitterness are produced so as to form a composite waveform $V_4$ shown in FIG. 3b, and these voltage waveforms $V_1'$ and $V_2'$ are applied in combination to the lingual papilla of the person, the sourness is sensed. In this case, the voltage waveforms $V_1'$ and $V_2'$ correspond to the equations (1) and (2) in which the constants $\tau_1$, $\tau_2$, C, $K_1$ and $K_2$ are made equal to 1.0000, 1.1111, 0.6, 13.5 and 12.2, respectively. Further, voltage waveforms similar to the voltage waveforms $V_1'$ and $V_2'$ are obtained even when the value of the constant c is changed over a range from 0.6 to 1.0. In either case, the voltage waveform $V_2$ or $V_2'$ is formed by adding an appropriate bias voltage to the voltage waveform produced on the basis of the equation (2), so as to make the sum voltage $V_1 + V_2$ or $V_1' + V_2'$ equal to zero at a time $t=0$.

It is known from the above that the saltiness, bitterness, sweetness and sourness can be electrically generated or synthesized by applying the voltage waveforms $V_1$ and $V_2$ corresponding to the equations (1) and (2), to the lingual papilla of a person individually or in combination. However, in order to cause a person to sense a taste continuously, it is necessary to apply the voltage having such a waveform to the lingual papilla repeatedly. As mentioned previously, a taste is strongly sensed at the rising or falling portion of a potential change having a time constant of 1.591 to 0.4550 and the 3 dB upper frequency of 0.1 to 0.35 Hz. Accordingly, it is desirable to generate the rising or falling portion of such a waveform repeatedly. In view of the time constant of the potential waveform, it is preferable to use a repetition period of about one second.

Figure 4:
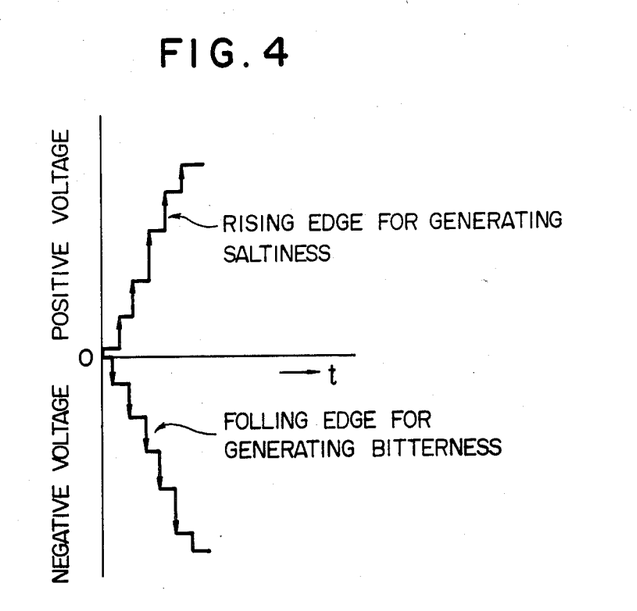
FIG. 4 is a graph showing microscopic changes in gustatory potential for generating the sense of taste.

Further, the following fact has been found by the study of gustatory-sense generating mechanism. That is, a substance having a taste does not produce a continuous gustatory stimulus at the rising or falling portion of the gustatory potential curve of the substance, when viewed microscopically. A gustatory potential curve corresponding to, for example, the saltiness or bitterness rises or falls stepwise as shown in FIG. 4, and the saltiness or bitterness is sensed at each rusing or falling edge. The fact suggests that when the gustatory sense is synthesized by voltage waveforms such as given by the equations (1) and (2), it is desirable to apply these voltage waveforms to the lingual papilla of a person not in a continuous manner but in a discrete manner. Further, it is known from the above fact that these voltage waveforms can be combined by applying voltages sampled from the voltage waveforms, to the lingual papilla. That is, when voltages sampled at an interval of, for example, 0.025 sec. from two voltage waveforms corresponding to a desired taste are applied to the lingual papilla, the gustatory sense is generated in a manner similar to the actual gustatory-sense generating mechanism.

Figure 5:
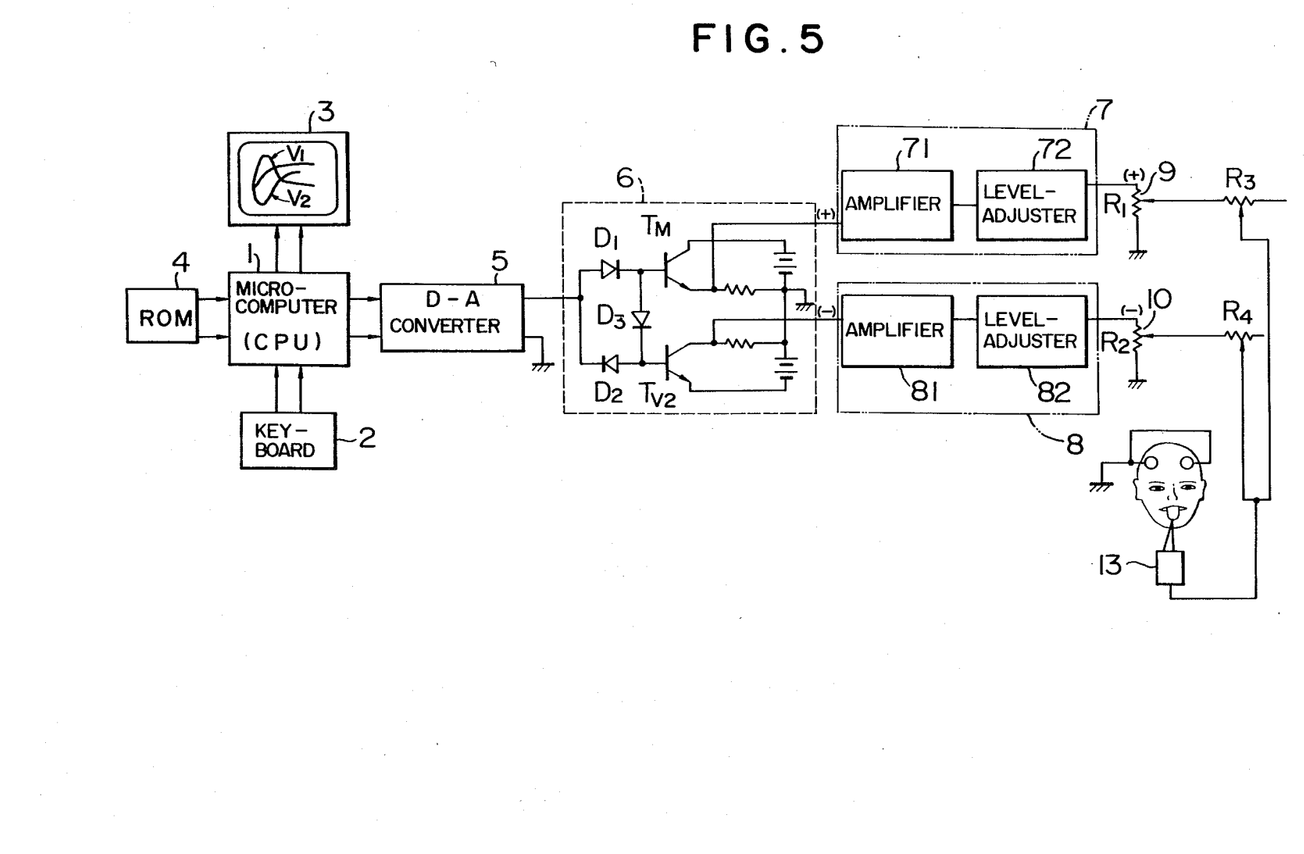
FIG. 5 is a block diagram showing the construction of an apparatus for carrying out the gustatory sense synthesizing method according to the present invention.
Figure 6:
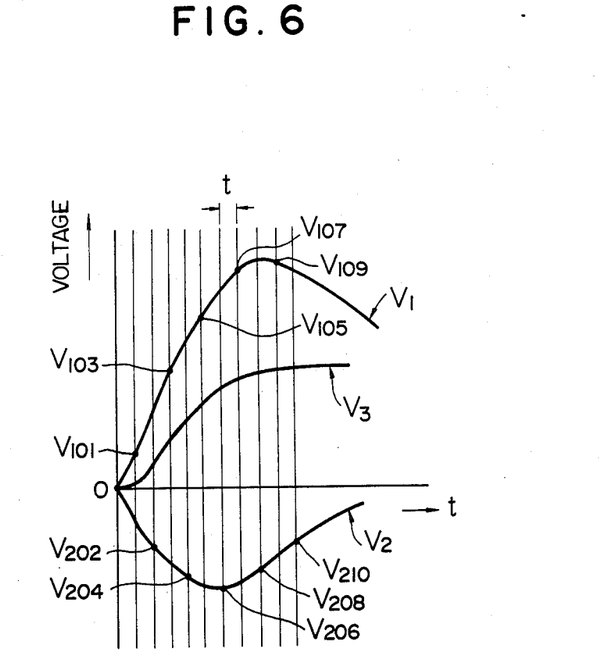
FIG. 6 shows that data is sampled from two potential curves alternately.

FIG. 5 shows an apparatus for electrically synthesizing the sense of taste, which is constructed on the basis of the above-mentioned thought. Referring to FIG. 5, a microcomputer 1 executes a program which is read out of an ROM 4 in accordance with an instruction inputted manually through the aid of a keyboard 2. The ROM 4 stores therein programs containing data such as voltage values sampled from voltage waveforms corresponding to the saltiness, bitterness, sweetness and sourness. For example, in a program CC for the sweetness, voltage values sampled alternately from the voltage waveform $V_1$ (corresponding to the saltiness) and from the voltage waveform $V_2$ (corresponding to the bitterness) at an interval of 0.025 sec. are arranged in the sampling order, that is, in the order of $V_{101}$, $V_{202}$, $V_{204}$, $V_{105}$, and so on as shown in FIG. 6. When the execution of the program CC is instructed, these voltage values are put in an RAM of the microcomputer 1 at predetermined addresses. Needless to say, the voltage waveforms $V_1$ and $V_2$ are formed so that the composite waveform of these voltage waveforms becomes equal to the potential curve $V_3$ corresponding to the sweetness. In each of a program AA for the saltiness and a program BB for the bitterness, voltage values sampled from one of the above voltage waveforms $V_1$ and $V_2$ at an interval of 0.025 sec. are arranged in the sampling order.

Now, explanation will be made on an embodiment of a method of electrically synthesizing the sense of taste according to the present invention.

Figure 7:
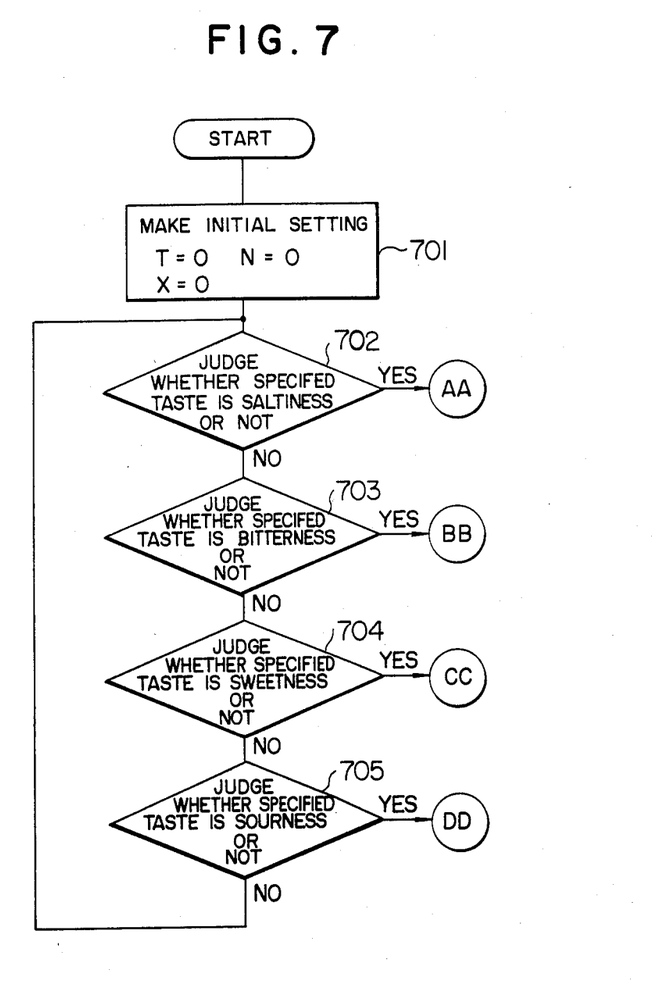
FIGS. 7 and 8 are flow charts each showing the processing carried out by the microcomputer of FIG. 5.
Figure 8:
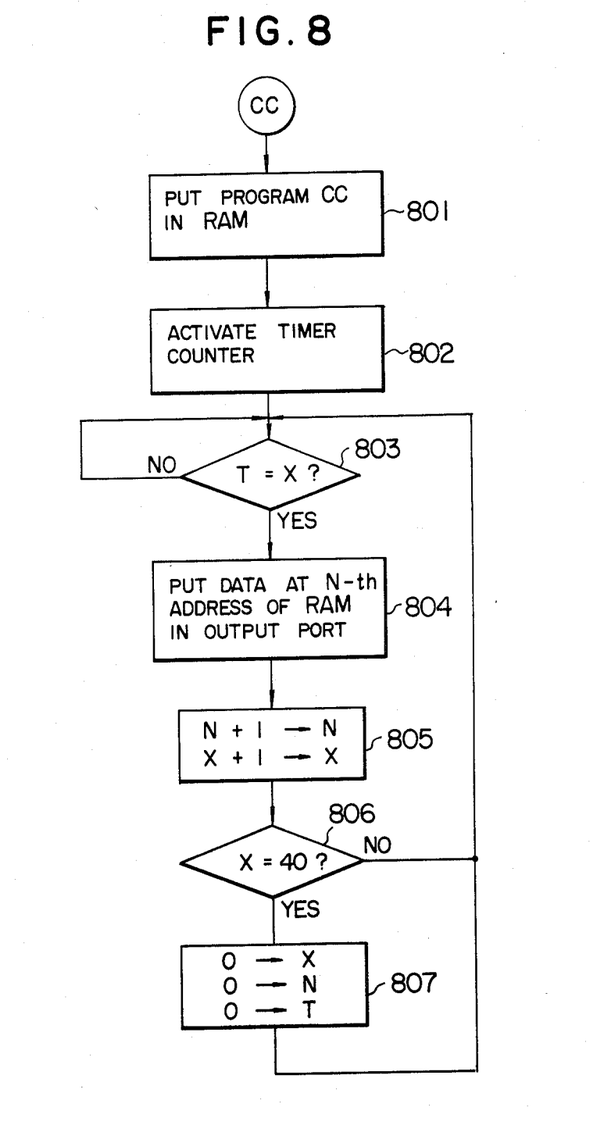

When a desired taste is specified and a start signal is generated through the aid of the keyboard 2, the computer 1 executes programs in accordance with the flow charts shown in FIGS. 7 and 8. As shown in FIG. 7, the initial setting is first performed in step 701. That is, the contents T of a timer counter, the address N of read-out data, and the number N of the sampling operation are all reset to zero. Next, steps 702, 703, 704 and 705 are executed in the order described, to judge which of the saltiness, bitterness, sweetness and sourness is the specified taste, and one of programs AA, BB, CC and DD is executed in accordance with the taste determined by the above judgement. In some cases, owing to an erroneous input operation or the malfunction of the computer 1, the specified taste may disagree with each of the saltiness, bitterness, sweetness and sourness. In such cases, the processing in the steps 702 to 705 is repeated. If the next program is not executed even after the above processing has been repeated many times, it is judged that a fault has occurred, and the operation of the computer 1 is manually stopped. Now, let us consider the case where it is judged in the step 704 that the specified taste is the sweetness, by way of example. After the processing in the step 704 has been performed, the program CC is executed in accordance with the flow chart shown in FIG. 8.

First, the program CC is fetched from the ROM 4 into the RAM which is provided in the computer 1 (step 801). Thus, the voltage values $V_{101}$, $V_{202}$, $V_{103}$, $V_{204}$, and so on shown in FIG. 6 are arranged at predetermined addresses of the RAM. (In the present embodiment, the storage address is designated by N, and the head address is indicated by zero.) Next, the timer counter provided in the computer 1 is activated (step 802). The timer counter has been reset to the initial value of zero, and is incremented by one at an interval of 0.025 sec. (equal to the sampling period) when activated. In step 803, the contents T of the timer counter are compared with the sampling number X. When T=X, the processing in step 804 is performed. When T is not equal to X, the processing in step 804 is not performed till the value of T becomes equal to the sampling number X. At the starting time of the operation, both of T and X are equal to zero, and therefore the processing in the step 804 is immediately performed. Thereafter, the processing in the step 804 is not performed until the value of T is increased by one. In the step 804, a voltage value sampled from the voltage waveform $V_1$ or $V_2$ is fetched from N-th address (starting from the zero-th address, namely, head address) of the RAM into the output port of the computer 1, and then delivered. Next, each the values of N and X is increased by one (step 805). In step 806, it is judged whether the increased value of X is equal to 40 or not. In the present embodiment, the composite voltage waveform is generated so as to have a repetition period of 1 sec., and the sampling operation is performed at an interval of 0.025 sec. Accordingly, the number of sampled data is equal to 40. That is, the sampling number X is given by 0, 1, 2, ... and 39. When the sampling number X starting from 0(zero) reaches 39, all of 40 data have been sampled. Accordingly, when the value of X is equal to 40, it is indicated that one repetition period of the composite voltage waveform has terminated. Then, the values of X, N and T are all reset to zero (step 807), to start the next period of the composite voltage waveform. When the value of X is not equal to 40, the processing in the steps 803 to 806 is again performed.

As mentioned above, in the case where the program CC is executed, data $V_{101}$, $V_{202}$, $V_{103}$, $V_{204}$, and so on are successively delivered from the computer 1 at an interval of 0.025 sec., and such a series of operations are repeated with a period of 1 sec. Referring back to FIG. 5, a digital output from the computer 1 is converted by a D-A converter 5 into an analog voltage, which is applied to a positive-and-negative separating circuit 6 to discriminate between positive and negative voltages. Positive output voltages (such as $V_{101}$ and $V_{103}$) and negative output voltages (such as $V_{202}$ and $V_{204}$) are amplified by amplifier units 7 and 8, respectively. The output voltage of the amplifier unit 7 is adjusted by a potentiometer 9 and a resistor $R_3$ so as to have an appropriate value, and the output voltage of the amplifier unit 8 is similarly adjusted by a potentiometer 10 and a resistor $R_4$. The output voltages thus adjusted are applied between a disc electrode 11 or 12 kept in contact with the temples of a person and a rod electrode 13 kept in contact with the lingual papilla of the person.

Each of the amplifier units 7 and 8 includes therein an amplifier 71 or 81 which is provided with a variable resistor for adjusting an output voltage, and a level adjuster 72 or 82 which is provided with a variable resistor for adjusting the zero position of the output voltage.

Figure 9:
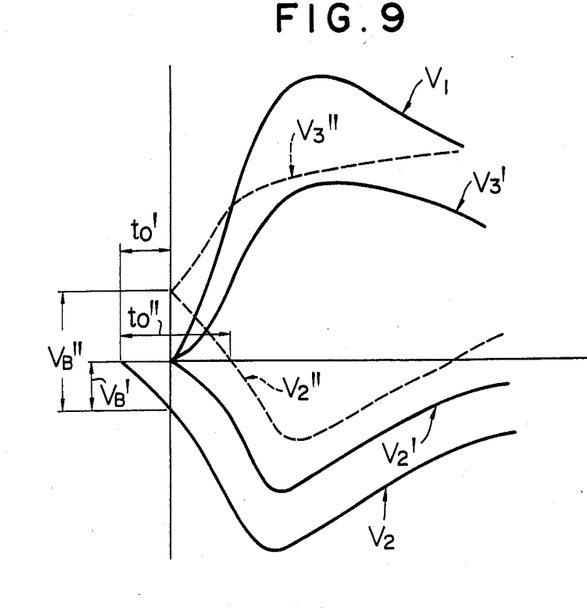
FIG. 9 is a graph showing a change in the composite waveform of two voltage waveforms generated by the apparatus shown in FIG. 5, caused by adding a bias voltage to one of the two voltage waveforms before the voltage waveforms are combined with each other.

The level adjusters 72 and 82 function as follows. When positive and negative voltage $V_1$ and $V_2$ which have been delivered from the positive-and-negative separating circuit 6 and amplified by the amplifiers 71 and 81, have different zero positions for some reasons and the zero positions are deviate from each other by a time $t_0'$ as shown in FIG. 9, a positive bias voltage $V_{B'}$ is added to the negative voltage waveform $V_2$ so that the sum $V_2 + V_{B'}$ (namely, a voltage waveform $V_2'$) and the positive voltage waveform $V_1$ have a voltage of zero at $t=0$. That is, when the bias voltage $V_{B'}$ is added to the voltage waveform $V_2$ to shift the negative voltage waveform $V_2$ in the positive direction, the bias voltage $V_{B'}$ is adjusted so that both of the shifted voltage waveform $V_2'$ and the positive voltage waveform $V_1$ have a voltage of zero at the time $t=0$. The voltage waveform $V_2'$ substantially corresponds to a voltage waveform which is obtained by shifting the phase of the negative voltage waveform $V_2$ by the time $t_0'$.

A voltage waveform $V_3'$ is obtained by synthesizing the voltage waveforms $V_1$ and $V_2'$.

Further, when a bias voltage $V_{B''}$ is added to the voltage waveform $V_2$ to form a voltage waveform $V_2''$, this voltage waveform $V''$ substantially corresponds to a voltage waveform which is obtained by shifting the phase of the voltage waveform $V_2$ by a time $t_0''$. A waveform $V_3''$ is obtained by synthesizing the voltage waveforms $V_2''$ and $V_1$. As mentioned above, when the bias voltage is varied, different compositive waveforms such as $V_3'$ and $V_3''$ are formed, and the gustatory sense caused by the composite voltage waveform is changed. That is, by adjusting the bias voltage, it is possible to follow the gustatory sense which varies slightly with persons.

Figure 10:
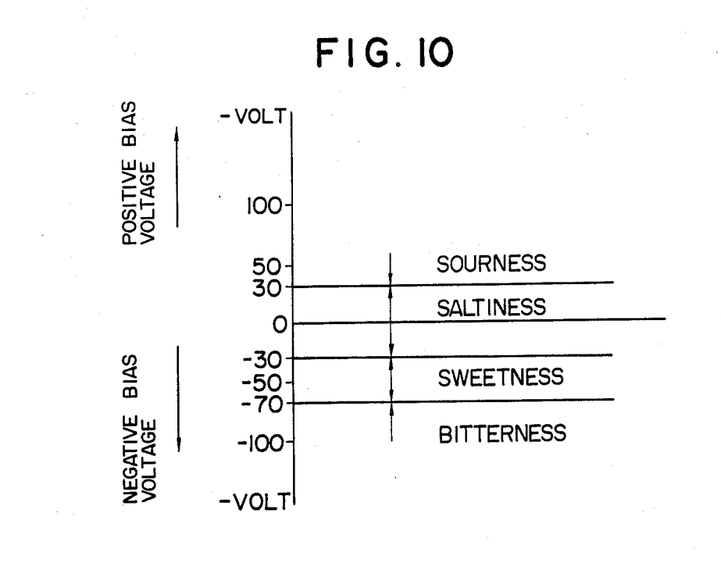
FIG. 10 is a view for explaining changes in gustatory sense caused by varying the bias voltage added to one of the voltage waveforms.

The adjustment of the bias voltage may be made for both of the voltage waveforms $V_1$ and $V_2$. However, only the bias voltage added to one voltage waveform (for example, the voltage waveform $V_2$) is usually adjusted. According to the apparatus shown in FIG. 5, the gustatory sense can be changed by varying the bias voltage $V_B$ added to the voltage waveform $V_2$ while keeping constant the voltage waveform $V_1$. In more detail, when the bias voltage $V_B$ is changed from $-100$ V to $+100$ V, the gustatory sense caused by the composite voltage waveform $V_3$ including the bias voltage $V_B$ is changed in the order of the bitterness, sweetness, saltiness and sourness, as shown in FIG. 10. As a matter of course, the bias voltage $V_B$ is varied with the waveform and phase of the output voltages $V_1$ and $V_2$ from the positive-and-negative separating circuit 6. However, the gustatory sense caused by the composite voltage waveform can be adjusted over a fairly wide range by varying the bias voltage.

Further, a television monitor 3 shown in FIG. 5 is provided for visually monitoring the gustatory potential curves $V_1$ and $V_2$ delivered from the computer 1, and for visually monitoring a potential curve $V_3$ or $V_4$ corresponding to the composite curve of the gustatory potential curves $V_1$ and $V_2$, if necessary.

In the above-mentioned embodiment, a value sampled from the potential curve corresponding to the saltiness, and a value sampled from the potential curve corresponding to the bitterness are alternately applied to the gustatory organ. However, it is not always required to apply these sampled values alternately, but a similar effect can be obtained by applying these sampled values simultaneously or at random.

I claim:

1. A method of electrically synthesizing the sense of taste, comprising:
    a first step of previously determining time-varying, gustatory potential curves representative of each of saltiness, bitterness, sweetness, and sourness;
    a second step of generating first and second voltage outputs, said first and second voltage outputs having substantially the same time-potential characteristics as said gustatory potential curves representative of saltiness and bitterness, respectively;
    a third step of performing a sampling operation for said first and second voltage outputs, and combining the sampled voltages so that a composite output of said sampled voltages has substantially the same time-potential characteristics as said gustatory potential curve representative of one selected from sweetness and sourness, to generate a third voltage output; and
    a fourth step of applying the third voltage output to the lingual papilla of a person.

2. A method of electrically synthesizing the sense of taste according to claim 1, wherein said third step includes a step of adjusting the level of voltages sampled from at least one of said first and second voltage outputs, and a step of combining the level-adjusted voltages with voltages sampled from the other voltage output.

3. A method of electrically synthesizing the sense of taste according to claim 2, further comprising a step of adjusting the voltage value of said third voltage output so as to obtain the voltage value to be applied to the lingual papilla of a person.

* * * * *